United States Patent [19]

Mitchell et al.

[11] Patent Number: 5,173,737
[45] Date of Patent: Dec. 22, 1992

[54] MEASUREMENT OF AVIAN EMBRYO MOVEMENT IN INTACT EGGS

[75] Inventors: Bailey W. Mitchell; Michael L. Perdue, both of Watkinsville, Ga.

[73] Assignee: The United States of America as represented by the Secretary of Agriculture, Washington, D.C.

[21] Appl. No.: 765,744

[22] Filed: Sep. 26, 1991

[51] Int. Cl.⁵ .............................................. A01K 43/00
[52] U.S. Cl. ................................................. 356/53
[58] Field of Search .................... 356/52, 53; 209/511, 209/577; 119/6.8

[56] References Cited

U.S. PATENT DOCUMENTS 3,540,824  11/1970  Fonda et al. ............................ 356/53

OTHER PUBLICATIONS

Bursian, A. V., The influence of light on the spontaneous movements of chick embryos, Bulletin of Experimental Biology and Medicine (Russian), vol. 58:7–11, Jul. 1964.

Hanson, R. P. and Brandly, C. A. Identification of vaccine strains of Newcastle disease virus, Science 122: 156–157, Jul. 1955.

Perdue, M. L., Wainright, P. W. and M. Bruch, Effects of Chicken Embryo age on time to death following infection by avian influenza viruses: implications for distinguishing highly pathogenic isolates, Virus Research 16: 137–152, 1990.

Norberg, John, "Chix in Space", Purdue Alumnus, May 1989, pp. 11 and 28–31.

Zakaria, A. H. "Effect of Fluorescent Light on Hatchability . . . " Poultry Science, 1989, 68:1585–1587.

*Primary Examiner*—Richard A. Rosenberger
*Attorney, Agent, or Firm*—M. Howard Silverstein; John D. Fado; David R. Sadowski

[57] ABSTRACT

The present invention provides measurement of avian embryo movement in intact eggs by: directing light into and through at least one intact avian egg, with light of sufficient intensity and duration to stimulate embryo movement, whereby portions of the light exit the at least one intact avian egg; sensing instantaneous intensities of the portions of the light exiting each of the eggs, and; determining a ratio of, range of sensed light intensities ($I_R$) to average sensed light intensities ($I_A$), for each of the eggs. The ratio of $I_R:I_A$ is a measure of avian embryo movement.

19 Claims, 9 Drawing Sheets

TOP VIEW (E = EGG, L = LIGHT)

EXPLODED VIEW OF LIGHT BOX

MEASUREMENT OF AVIAN EMBRYO MOVEMENT IN INTACT EGGS

FIELD OF THE INVENTION

The present invention is drawn to apparatuses and processes for measuring avian embryo movement in intact eggs. Measurements made in accordance with the present invention are particularly advantageous in that they are non-invasive and nondestructive.

BACKGROUND AND SUMMARY OF THE INVENTION

The developing chicken embryo has been a subject of study since the development of the methods of scientific inquiry. The earliest known detailed description is credited to Aristotle (384-322 B.C.) and a host of other treatises were presented through the ages culminating perhaps in the classical, elementary, english-language treatise "The Development of the Chick" by Frank R. Lillie in 1908. The gross anatomical and microscopic observations of the avian embryo have been almost universally accepted as model observations for embryonic development in general. Numerous texts exist which carefully outline the stages during the 21 day incubation period of the chicken embryo and perhaps the most comprehensive and widely used of these has been "The Avian Embryo" by Alexis L. Romanoff (1960).

Remarkably, however, even this text mentions nothing of the phenomenon of spontaneous movement of embryos within the egg. It has been noted by anyone who has observed developing embryos under strong light (candling), that they move in irregular jumps or spasms as early as the 6th day of incubation up through hatching. Presumably this movement has been accepted as a simple, common occurrence in embryo development and little empirical work on spontaneous movement has been published in contemporary scientific literature. One study (Bursian, A. V., 1964, Bulletin of Experimental Biology and Medicine {Russian}; Vol/58, pp 7-11) demonstrated that embryos removed from the shell and connected to movement sensors, responded to light stimulus and exhibited greater spontaneous movement than when not in the presence of light. It is not clear how this relates to in-ovo development however, and no work could be found which actually answers the question of whether embryos move in response to the candling light or whether the embryo moves continuously and candling only illuminates the movement. The consensus from exhaustive personal communications with poultry and avian scientists is that light does stimulate movement of the developing embryo.

The candling of eggs to detect movement has provided a qualitative mechanism for determining whether an embryo is alive or dead or perhaps even "sick", following inoculation of a variety of avian pathogens. In particular, with one avian virus, Newcastle disease virus (NDV), the rate at which the virus kills the embryo has been shown to be directly related to the virulence of the particular strain of virus (Hanson, R. P. and Brandly, C. A., 1955, Science 122, 156–157). That is, the faster the strain kills the infected embryo, the more likely the virus is to be highly lethal in an infected adult bird. This observation has been adapted to provide a diagnostic application for use in identifying highly virulent isolates from field strains of NDV. The procedure involves a staggered inoculation schedule and requires qualitative human assessment at regular time intervals of whether an embryo is alive or dead, based on its response under candling conditions. An averaged "mean death time", (MDT), is then derived for each viral isolate and the number is a reflection of the isolates virulence.

A slightly different, but related approach has been recently developed for the avian influenza (AI) viruses (Perdue, et. al., 1990, Virus Research 16, 137–152) and it may be possible in the future to use a similar diagnostic protocol for the avian influenza field strains.

The present invention avoids the disadvantages of the prior art and provides very significant improvement over the aforementioned procedures, as it permits:

elimination of human qualitative judgments involved in interpreting observations made during manual candling, higher sensitivity of measurements than was previously possible, automation of measurements, analysis and data recording, more frequent and rapid measurements and data processing than manual procedures, electronic sensing of embryo movement, rapid and accurate automated quantification of the amount of embryo movement, rapid and accurate automated measurement of the frequency of embryo movement, rapid and accurate automated measurement of the pattern of embryo movement, non-invasive and nondestructive measurement of embryo movement, elimination of the need to remove incubating eggs from an incubator to take such measurements and elimination of the adverse effects of manual handling of the eggs.

These and other objects and advantages of the present invention, which will become readily apparent from the ensuing disclosure, are achieved by:

directing light into and through at least one intact avian egg, wherein the light is of sufficient intensity and duration to stimulate embryo movement, whereby portions of the light exit the at least one intact avian egg, sensing intensities of the portions of the light exiting each of the at least one intact avian eggs, determining a ratio of, range of sensed light intensities to average sensed light intensities, for each of the at least one intact avian eggs. The aforementioned ratio being a measure of avian embryo movement.

The present invention has wide applicability, including for example: (1) in poultry disease research, for assessing the effects of various inoculants on avian embryos in intact eggs (the ability to rapidly and automatically determine embryo viability at any reading interval would most certainly open avenues which have not yet been opened for investigators in avian diseases and in poultry science studies, e.g. determination of viral pathogenicity on embryos, measuring the effects on virulence of mixing closely related variants of the same strain of virus which differ in pathogenicity i.e. the biological scenario most likely approximating a natural disease outbreak); (2) in hatcheries for determinations of embryo viability in order to sort eggs containing viable embryos from eggs containing non-viable embryos e.g. as an alternative to incubating all of the eggs without screening which results in the incubation of some non-fertile eggs; (3) for detailed studies of movement in developing embryo (classical embryology studies) e.g. if automated determination of gender of developing embryos based on embryo movement could be accomplished, it would revolutionize the breeder industry and primary breeders which presently have to use specialists to determine the gender of 1 day old chicks (it is believed that range frequency and ratio of light intensity for embryonated eggs may be correlated to gender).

Since the present invention may be automated, when it is used with an egg incubator means (i.e. means for incubating at least one egg) it is not necessary for the eggs be removed from the incubator, or that the incubator be opened, when measurements of embryo movement are taken, as is necessary with manual candling techniques. Analogously, the present invention avoids the necessity to enter (or repeatedly enter) into high containment areas to assess embryo viability. Avoiding the necessity to directly access or manually handle the eggs is highly desirable since it eliminates the potentially disruptive effects caused by manual handling (e.g. a drop in incubator and/or egg temperatures for several minutes during and following candling and potential changes in activity or movement caused by the handling).

BRIEF DESCRIPTION OF THE DRAWINGS

FIG. 2A is the electronic circuit for the phototransistor sensors used in the system in FIG. 2.

DETAILED DESCRIPTION OF THE INVENTION

The present invention is based on the fact that embryo movement inside a backlit egg will cause light level changes at the surface of the shell. The amount of light reaching a particular position on the shell can be accurately determined with an electronic light sensor when ambient light levels are kept very low or completely dark.

FIG. 1 illustrates the basic components of a system of the present invention. One or more intact eggs may be held by egg holder means 1. Suitable egg holder means include, for example, a ventilated sheet metal box with 1.5" diameter holes 2.5" on center which has soft compressible cushions around each hole to help minimize light leakage around the edge of the egg. Light source means 2 functions to direct light into and through each of the intact avian egg(s). The light source means should provide light of sufficient intensity and duration to stimulate embryo movement. The preferred minimum light intensity is about 7,000 lux. Typical light intensity is from about 7,000 lux to about 15,000 lux. The duration may typically be at least about 10 seconds, as this will result in good movement which will continue indefinitely as long as light is directed into the egg(s). One of ordinary skill, having read the present disclosure, will be enabled to determine appropriate light intensity and duration, by experimentation with different light source means/intensities/times while monitoring embryo movement. More specifically, light source means which may be employed in the present invention include: incandescent, fluorescent and halogen sources, with a suitable power source, and optionally, controls. Preferably, the light source means should have the ability to produce at least about 7,000 lux at a distance of about 3 inches. Fluorescent light sources are preferred due to their higher efficiency and resulting cooler operation, which is less likely to heat the egg(s). Halogen and incandescent bulbs are available which can be powered by direct current (d.c.) batteries. Incandescent and fluorescent bulbs are available for use with alternating current (a.c.) power. The choice of power source is not critical, but certain embodiments of the present invention may utilize a.c. power for several other components, and the fluorescent bulbs are preferred for their cool operation, an a.c. powered light source is preferred for said embodiments. Portions of the light from the light source means 2 will exit each intact avian egg(s) and may be sensed by light intensity sensor means (LISM) 3. Such LISM which are suitable for use in the present invention include: photomultiplier tubes, phototransistors, photodiodes and Cadmium-Sulfide sensor means. Optionally the light source means 2, egg holder means 1 and LISM 3 may be contained within an egg incubator means or containment area, represented in FIG. 1 by rectangle 15, whereby the present invention may be carried out without removing the egg(s) from the egg incubator means or containment area. The output of the LISM is directed to a determining means 4 for determining the ratio of, range of sensed light intensity ($I_R$) to average sensed light intensity ($I_A$) i.e. the ratio of, $I_R$:$I_A$) for each egg that is evaluated in accordance with the present invention. This ratio is related to embryo movement, and determination of this ratio is critical to the present invention, because its use reduces the variability of activity levels, i.e. range of measured light level across time, and because it has been found to minimize the effects caused by differences in measured light level caused by parameters other than embryo movement (e.g. differences in egg shell thickness, embryo position, light level available at the egg and sensor differences). As described more fully herein after it has been found convenient to multiply the aforementioned ratio by 100 and name it "Ratiohat". Therefore $$\text{Ratiohat} = \frac{I_R}{I_A} \times 100 =$$

-continued $$\frac{\text{(Range of sensed light intensity)}}{\text{(Average sensed light intensity)}} \times 100.$$

Figure 1:
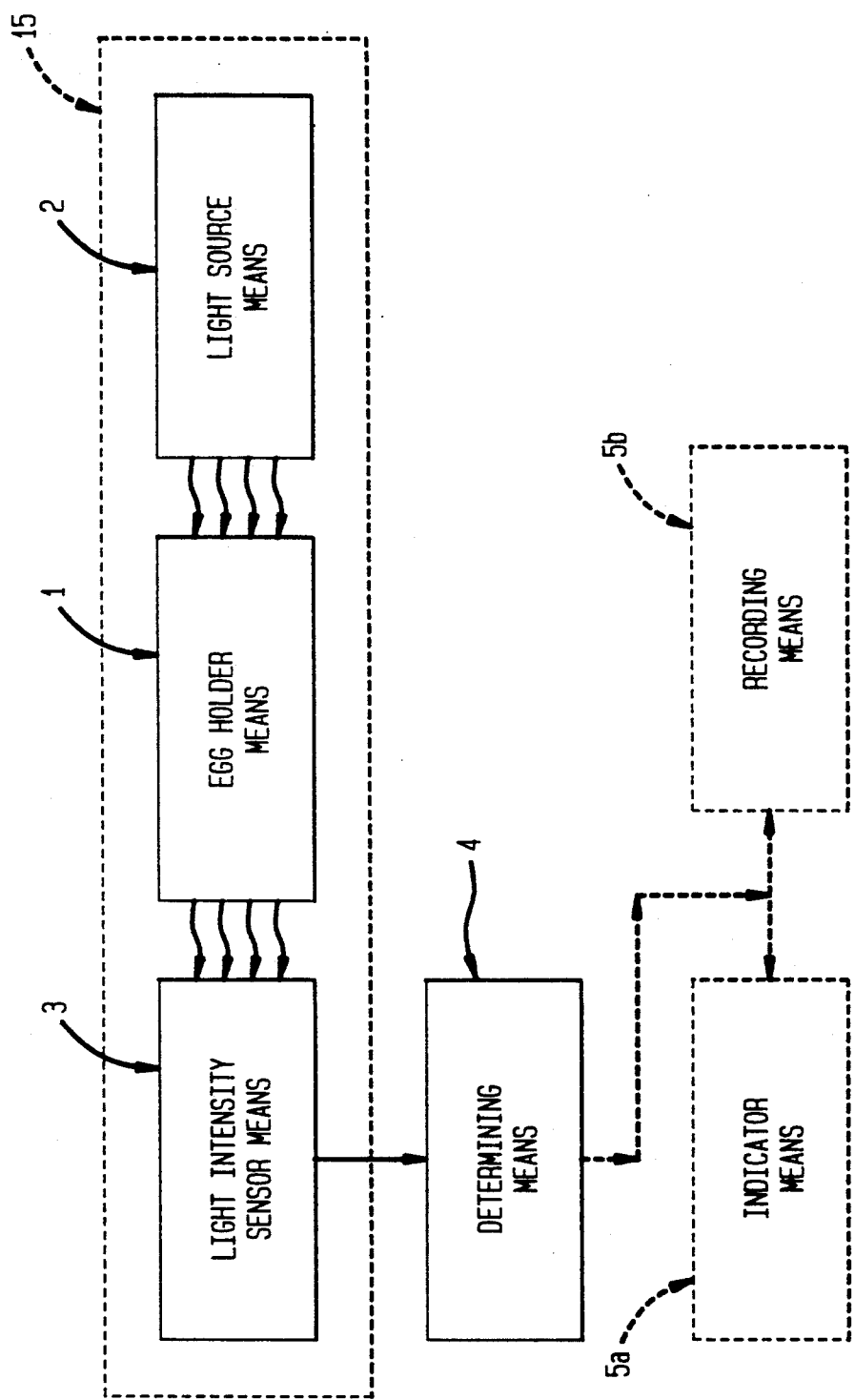
FIG. 1 is a schematic diagram of basic components which may be employed in the present invention.
Figure 2:
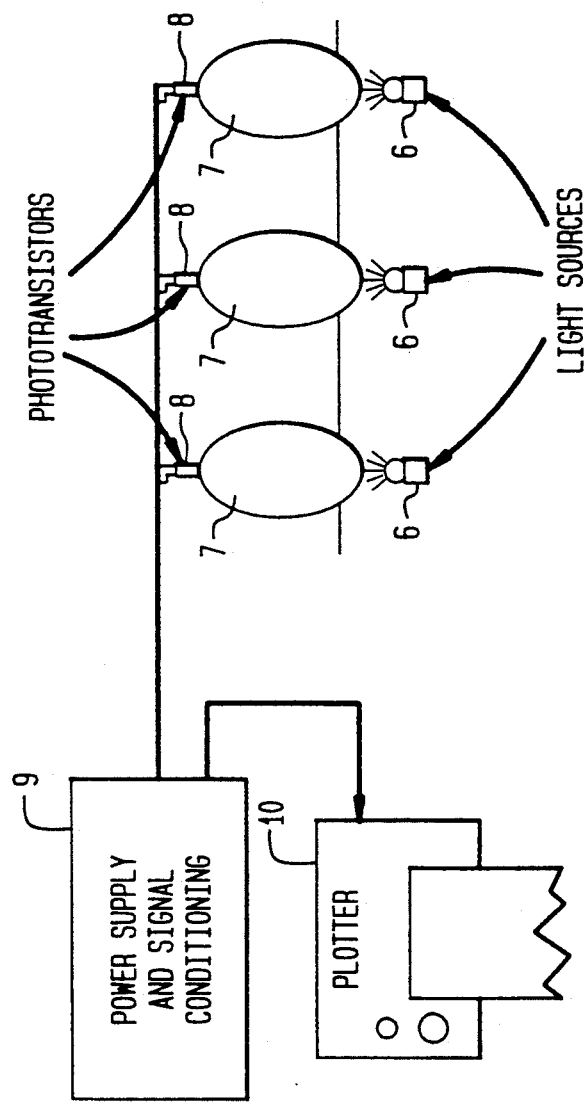
FIG. 2 is a schematic diagram of an example of a system of the instant invention.

Throughout the present specification and claims: "Range of sensed light intensity" ($I_R$) refers to the difference between the maximum instantaneous sensed light intensity and the minimum instantaneous sensed light intensity during the sampling period, i.e. ($I_I$ maximum - $I_I$ minimum)=$I_R$ and "Average sensed light intensity" ($I_A$) is defined as the average of all the light readings for a given egg during the sampling period. Typically, 50 samples were taken during a 5–10 second sampling period. The use of the ratio "Ratiohat" rather than an absolute range of the activity signal, proved to be beneficial in normalizing the data which tended to vary considerably in absolute amplitude due to differences in parameters such as egg shell thickness, position of the embryo, and placement of the sensor. Although the Ratiohat $<=2.0$ criteria for embryo death seems to work well, other factors such as slope change in the Ratiohat curve may be considered as tools for discriminating viral pathogenicity. The change in average sensed light intensity $I_A$ with time provides two unexpected results which have been beneficial. This variable decreases with increasing age of growing embryos i.e. light level corresponds inversely to the growth of the embryo (due to increased blockage of light by larger embryos), and it is significantly higher for non-fertile eggs (due to the reduced tissue mass inside the egg). The change in average sensed light intensity $I_A$ with time tends to be noticeably less with infected embryos than with non-infected embryos since the infected ones grow more slowly, if at all. Specific devices which may be employed as the determining means 4 include: a digital computer (e.g. micro-computer or PC), or an analog computer. The ratio of $I_R:I_A$ (or some value indicative thereof e.g. Ratiohat) is directed from determining means 4 to output means 5. This ratio, and optionally the instantaneous light intensities, may be output by output means 5 which may, for example, be: (1) visual display means, such as, a strip chart recorder, video monitor, LCD display, meter, gauge, etc.; (2) audio output means, e.g. speaker, headphones, etc.; (3) recording means, which may record the data for later utilization. FIG. 2 illustrates a specific example of a system of the present invention, generally of the type described above. More specifically, in the system of FIG. 2, the light source means takes the form of plural light sources 6 (e.g. hand-held candling lights which backlight each egg), which direct light into and through eggs 7. The light intensity sensor means (e.g. infrared phototransistors) 8, sense the intensities of the light exiting each of the eggs (at the surface of each of the eggs). The output of the externally powered phototransistors is directed to signal conditioning means 9. Suitable power supply and signal conditioning means include for example a 9 volt d.c. battery and circuit as shown in FIG. 2A. In addition, it may be desirable to amplify, attenuate, or filter the phototransistor output. The output of means 9 is directed to suitable output means, which may, as illustrated in FIG. 2, take the form of a plotter 10. With one specific system, constructed in accordance with FIG. 2, voltage changes with time of up to approximately 50 millivolts were obtained with embryos from 6 to 12 days of age. The output of this system varied considerably in amplitude (from 2 to 100 millivolts) depending on: (1) the position of the sensor against the egg; (2) the age of the embryo, and; (3) the power supply voltage.

Figure 3:
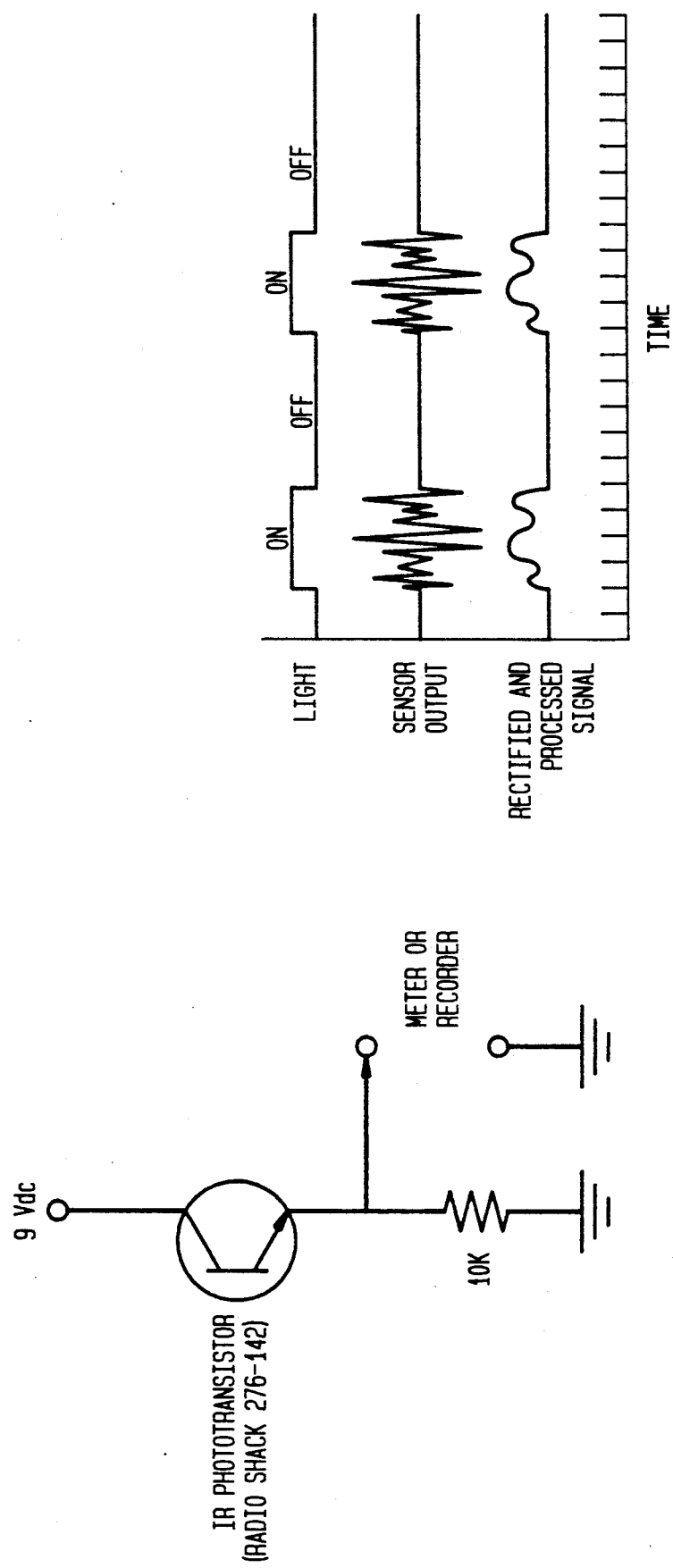
FIG. 3 is a graph of: candling light operation, sensor output, and rectified and processed signal vs. time (no specific units for the values illustrated); illustrating typical operation and outputs.

FIG. 2A illustrates the electronic circuit which was utilized with the phototransistor sensors in the system of FIG. 2. FIG. 3 is a graph of candling light operation, sensor output and rectified and processed signal vs. time, illustrating typical light operation, output and signals, for the system illustrated in FIGS. 2 and 2A. The rectified signal could be integrated using an integrator which would reset when it's output reached a preset value. By activating a counter each time the integrator reset, the signal could be quantified. A Ratiohat could be computed with analog computer components.

Figure 4:
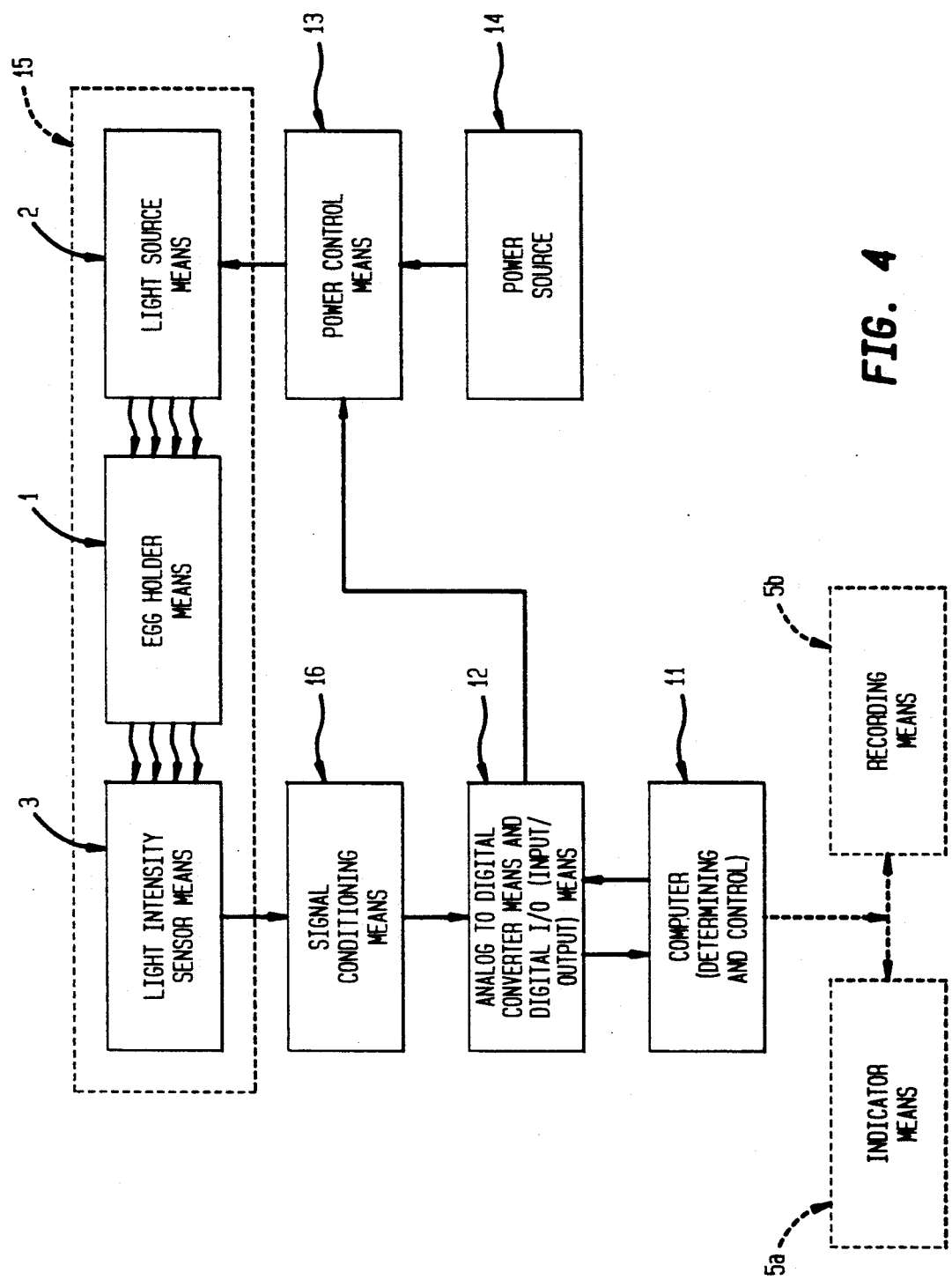
FIG. 4 is a block diagram of an automated system of the present invention.

FIG. 4 illustrates a more automated embodiment of the present invention wherein a computer 11 receives the output of the LISM 3 and: (1) functions as the determining means, for determining (e.g. computing or calculating) for each egg the ratio of $I_R$ to $I_A$; (2) communicates with the indicator means 5a and/or recording means 5b (for outputting the ratio $I_R$ to $I_A$, and optionally the instantaneous light intensities); (3) exchanges signals with analog to digital converter means (ADC means) 12 (i.e. means for converting analog electrical signals to digital electrical signals) and digital I/O (input/output) means. The LISM 3 may communicate with the ADC means 12 via signal conditioning means 16. The signal conditioning means 16 provides filtering, amplifying and/or attenuating of the analog signal from the sensor, so that the effects of frequencies outside the frequency of interest (i.e. noise) are minimized, and the signal will be within an acceptable voltage range for the ADC means. The computer provides control of the operation of the light source means by sending a digital control code to one of the digital outputs on the ADC means. The digital output (e.g. 5 volt logic level) is then sent from the ADC means to power control means 13 (e.g. a solid state relay). Thus, the computer may be programmed to automatically operate (via ADC means 12) the power control means 13, in order to automatically control provision of power from power source 14 to the light source means 2. Examples of ADC means which may be employed in the present invention include: an ADC-1 with 16 channels of analog input, 6 digit outputs and 4 digital inputs; analog and digital Optomux I/O boards from Opto 22, or; any one of many other analog and digital computer interface boards which are commercially available. Suitable power control means include, for example: Solid state relays, conventional electromechanical relays with a transistor or MOSFET driver to permit it to be operated by the low power digital output (if needed).

Figure 5:
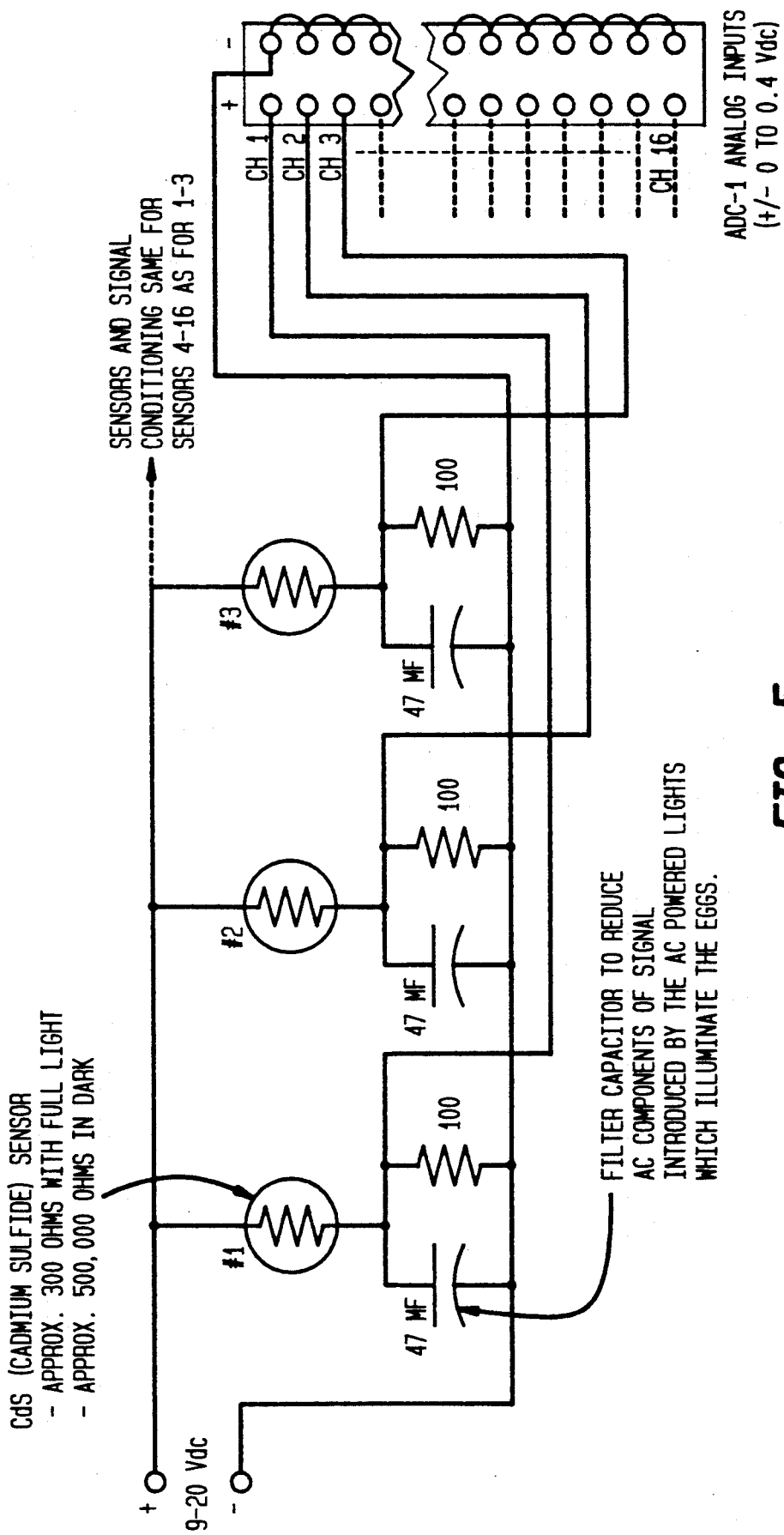
FIG. 5 shows a basic electronic circuit of the present invention employing Cadmium Sulfide sensors, with sensor outputs connected to low pass filters which are connected to an ADC-1 analog input device.
Figure 6:
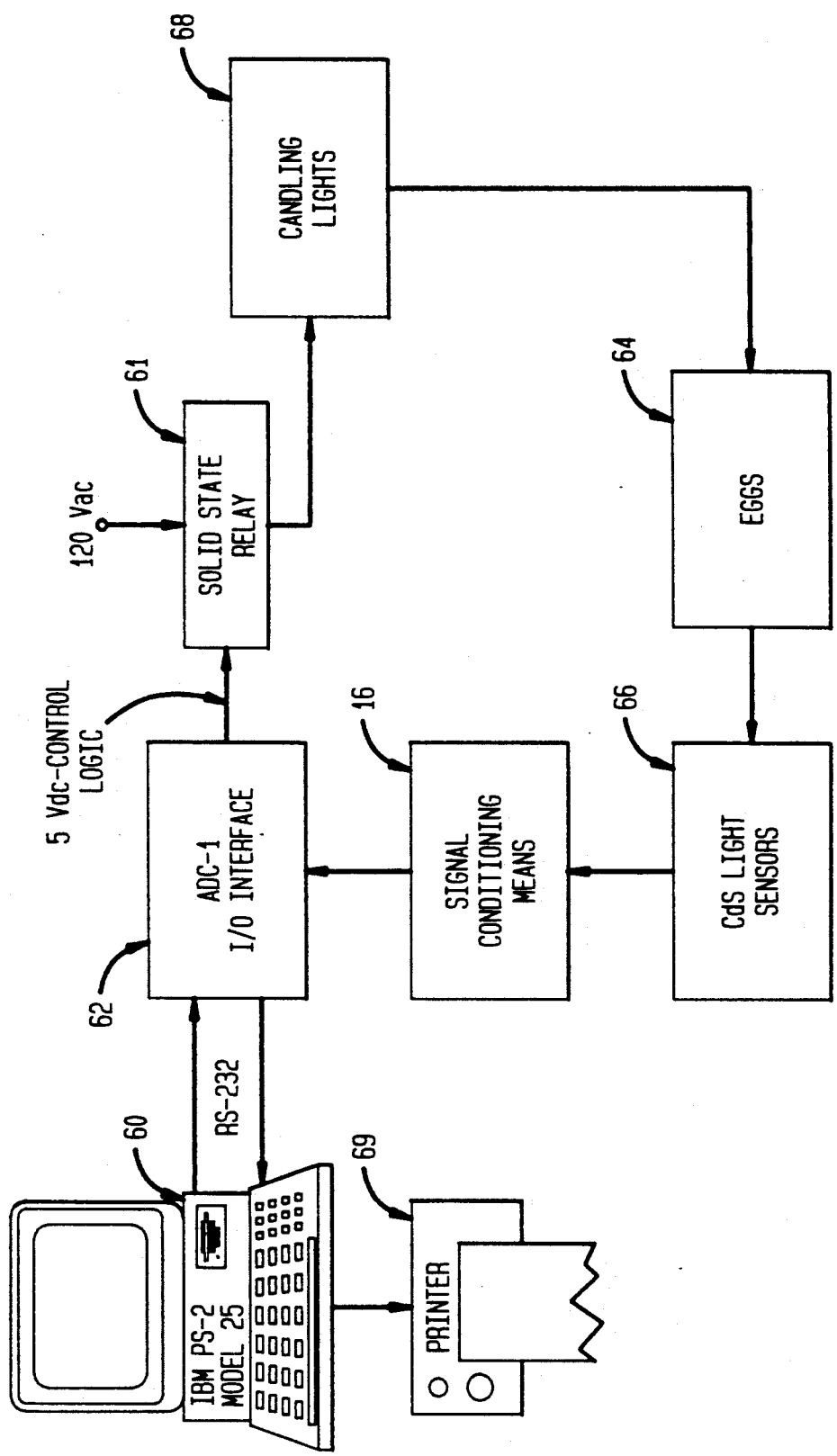
FIG. 6 is a block diagram of an automated system of the present invention utilized in examples 1 and 2.
Figure 7:
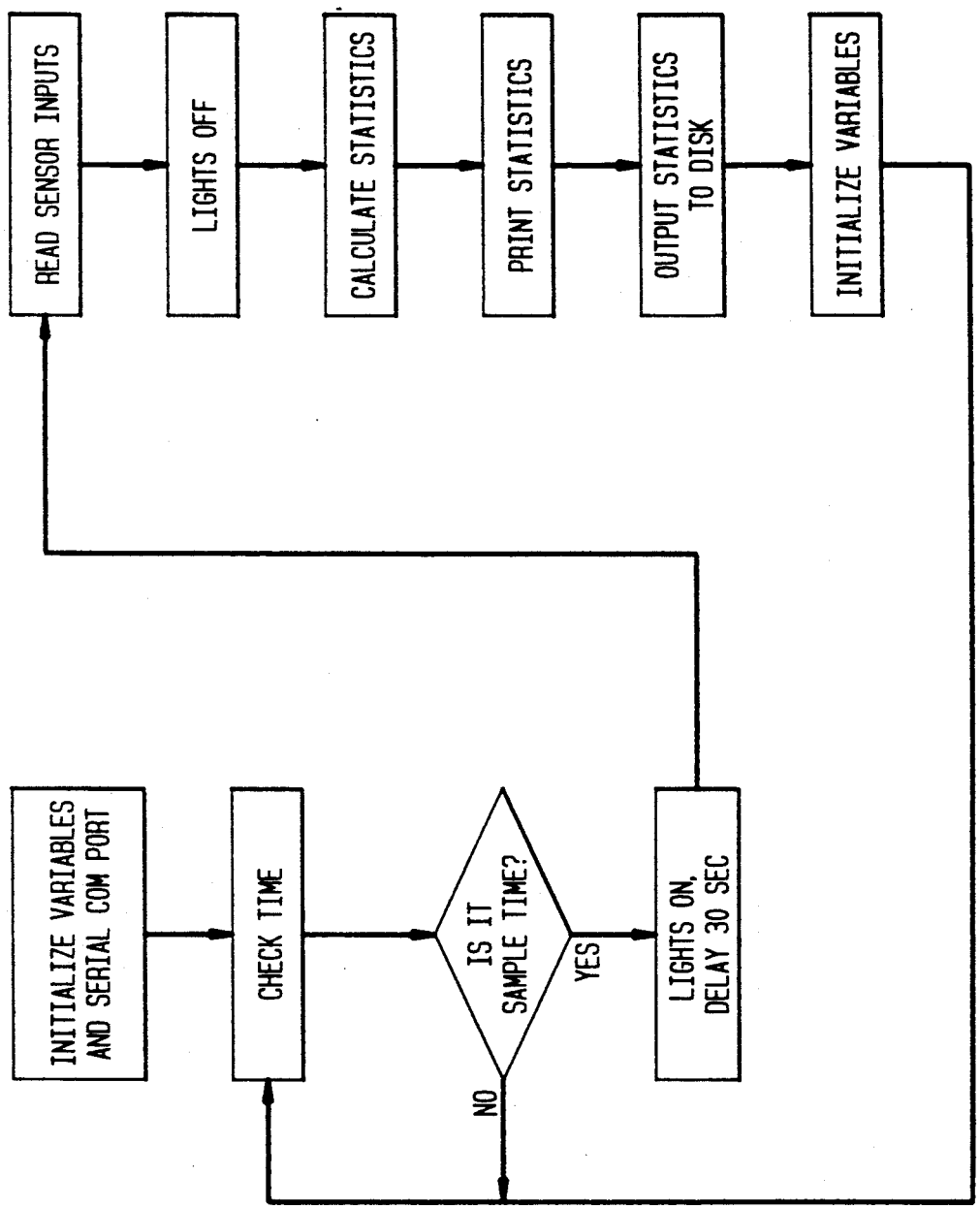
FIG. 7 is a flow chart for a data acquisition and control computer program of the instant invention.

It has been found expedient to: (1) increase the output voltage of the LISM (thus improving the signal to noise ratio), and; (2) increase the contact area of the LISM with the egg(s); by use of the Cadmium-Sulfide (CdS) sensors and electronic circuitry as shown in FIG. 5. In one specific example, such CdS sensors have a light pickup area of about 30 square millimeters compared to an area of only about 12.5 square millimeters for phototransistors. The larger area and higher output of the CdS sensors resulted in voltages at least 10 times greater than those obtained with phototransistors. Using this improved sensor, a complete monitoring, recording and light control system was developed, as shown in FIG. 6. An IBM PS-2 Model 25 microcomputer was used to: (1) control candling lights via solid state relay 61 and ADC-1 I/O Interface 62; (2) to read light levels via a standard serial communication link for digital computers designated "Electronics Industries Association RS-232," Washington, D.C., ADC-1 I/O Interface designated 62, signal conditioning means 16 and CdS light sensors 66; (3) to process and store data on disk, and; (4) to print results using printer 69; using a BASIC program, the flow chart for which is shown in FIG. 7. Data stored on disk may be further analyzed with Statistical Analysis System (SAS) to generate treatment averages, statistics and plots. The use of a computer to control lights and read sensors permits unattended operation and monitoring. The computer was able to restart automatically into an operating BASIC control program following a power outage by use of a battery backed clock in the computer and an autoexecute program.

Figure 9:
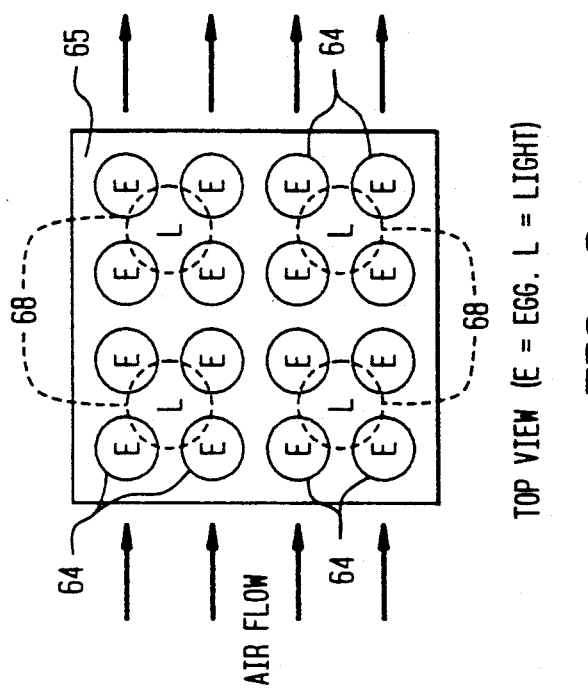
FIG. 9 is a top view of the device shown in FIG. 8.
Figure 8:
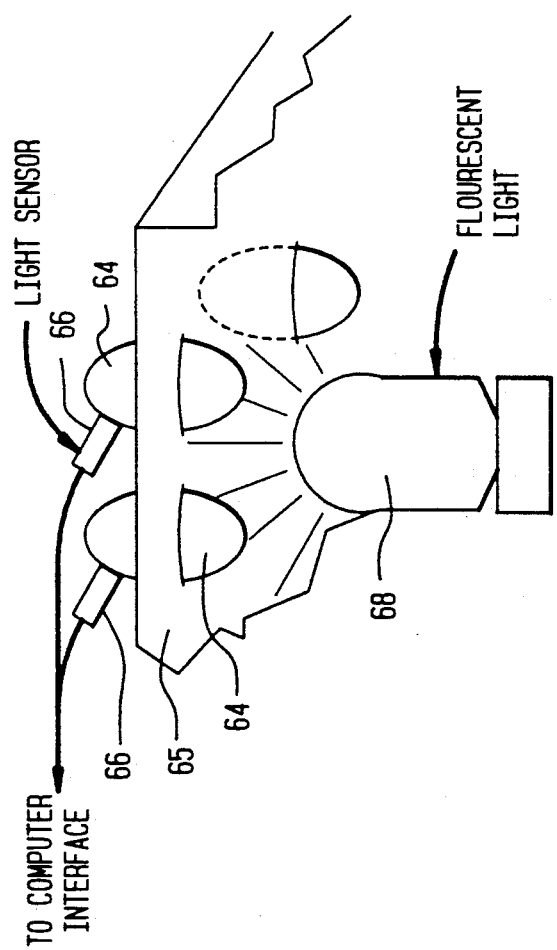
FIG. 8 shows a side view of a cutaway portion of a device for backlighting eggs in accordance with the present invention.
Figure 10:
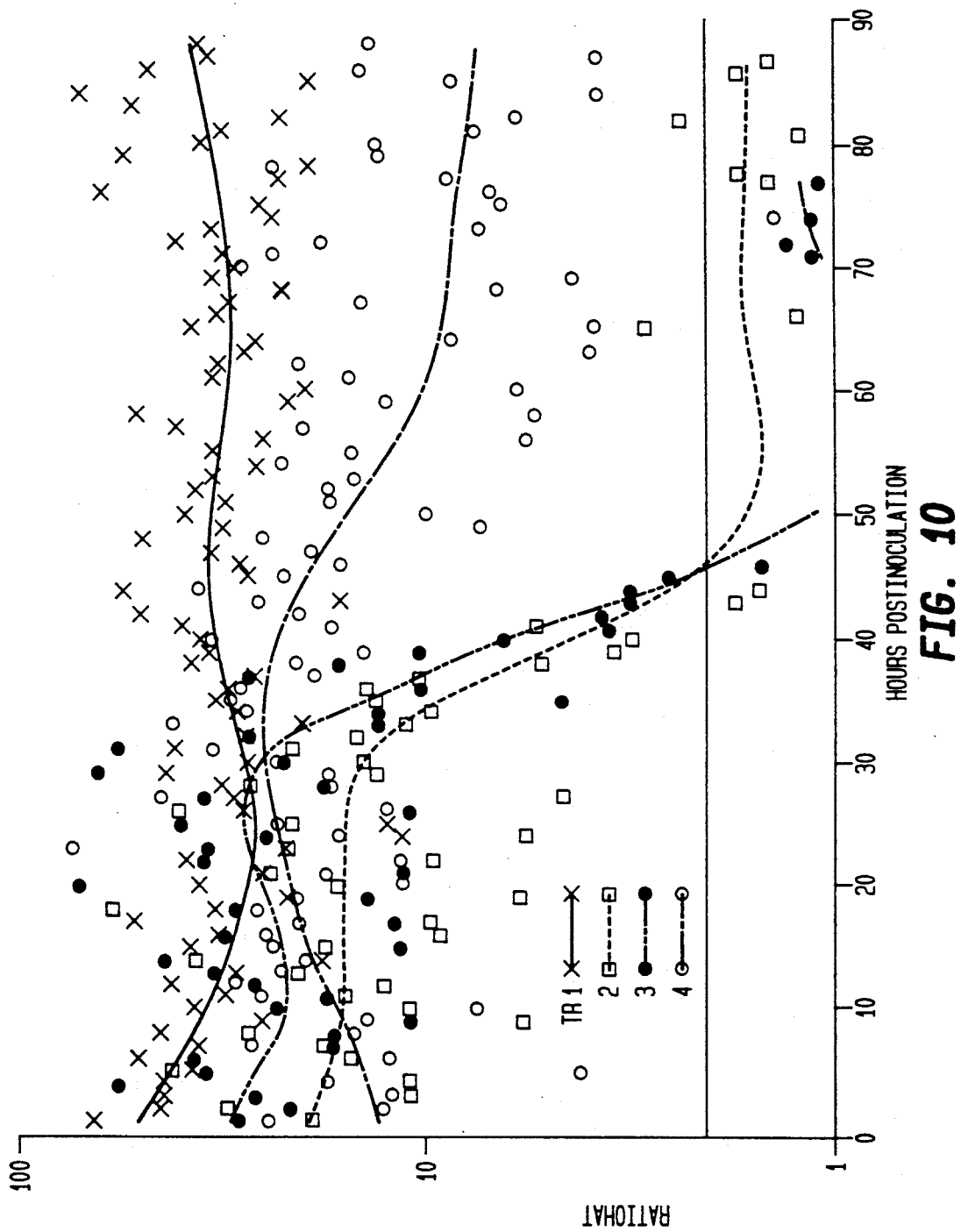
FIG. 10 is a graph of Ratiohat (i.e. (range of sensed light intensity $\times$ 100) $\div$ (average sensed light intensity) vs. time (i.e. hours postinoculation) for four different strains of influenza virus, as described in Example 2.

Inputs and outputs to the computer were accomplished with an ADC-1 interface device 62 which was capable of reading 16 analog inputs and controlling 6 digital outputs. The specific interface device used was an ADC-1 Data Acquisition and Control System, available from Remote Measurement Systems, Inc., Seattle, Wash. Alternatively, devices such as Optomux 16 channel analog input boards and 4 channel digital output boards from Opto 22, Huntington Beach, Calif., may be used. Four 15 Watt bulb-type fluorescent lights 68 were used underneath the eggs 64 in a continuously ventilated light box 65 (side view shown in FIG. 8, and top view shown in FIG. 9) to backlight them. Lights which may be employed in practicing the instant invention include for example 15 Watt Compax from General Electric, Cleveland, Ohio. Earlier tests with incandescent lights resulted in excessive temperature rises in the light box due to the heat the lights gave off, consequently where adequate ventilation or temperature control is not utilized, it is preferred to use fluorescent lights rather than incandescent lights. As previously indicated, the lights were controlled with a solid state relay 61. The specific relay used was a Crydom D1210 Solid State Relay from International Rectifier, El Segundo, Calif. Also, relays such as the SSRT-12D10 Solid State Relay from Potter and Bruinfield, Princeton, Ind., may be utilized in practicing the present invention. The temperature and humidity of the environment surrounding the test eggs was maintained by conventional commercially available incubator controls. For example, any commercially available thermostat with 0.5° F. deadband and range covering 95°–101° F., and humidistat with ability to control relative humidity from 50–70% would be suitable for use in the present invention.

By measuring the instantaneous light intensity $I_I$ with CdS light sensors 66 located just below the airspace of the eggs (such that the top of the light sensitive portion of the sensor was at, or not more than, about ⅛" below, the airspace of the egg) at about 6–8 times per second for 5–10 seconds, it was possible to acquire and store quantitative data from which activity level and frequency of movement of the embryos could be determined. In a typical experiment, the four candling lights were turned on for approximately 160 seconds at the first part of each hour (for one light box with 16 eggs) and activity determinations were made.

The following examples are intended only to further illustrate the invention and are not intended to limit the scope of the invention as defined by the claims.

EXAMPLE 1

A system of the present invention as shown in FIG. 6 and described herein above, was constructed and evaluated to determine if it could distinguish eggs with live embryos from eggs with dead embryos. Several experiments were conducted with the system using eggs containing embryos from 6 to 18 days of age, looking at the effect of aging with no virus present, sensor output values of brown eggs vs. white eggs, and the influence of different strains of influenza virus on embryo activity. Frequent visual observations confirmed the identification of eggs containing active and dead embryos. Preliminary tests indicated that the time at which Ratiohat values fell below a cutoff value of 2.0 corresponded closely to embryo death.

A multiplexer and another light box were added to permit two ADC-1 computer interface devices (like the one shown in FIG. 6) to be interfaced to the computer so that 32 eggs could be monitored, however the apparatus of the present invention could easily be expanded to test thousands of eggs by adding additional communication port multiplexers, computer interface boards and light boxes.

EXAMPLE 2

In this example four slightly different strains of the same influenza virus were inoculated into sets of 4 eggs containing live embryos at 0 time. The system shown in FIG. 6 recorded the embryo activity over a 90 hour period at hourly intervals. The following four different viruses were used: TR1 a non-pathogenic strain of the Pennsylvania 1983 H5N2 influenza isolate; TR2 a highly-pathogenic field isolate of the 1983 H5N2 outbreak; TR3 a highly-pathogenic laboratory isolate of the H5N2 strain, and; TR4 a second laboratory strain, which although highly pathogenic, is not as pathogenic as the strains represented by TR2 and TR3. The pathogenicity of all these viruses was also determined in young and old chickens. The results of the embryo experiment are shown in FIG. 10.

The results show that results of the animal pathogenicity studies can be mimicked by analyzing the effects on infected embryos. The non-pathogenic virus isolate had little effect on the embryos' activity as shown by the upper curve in FIG. 10. The most pathogenic isolates (TR2 and TR3) however clearly affected the embryos' activity, i.e. killing the embryo by 48 hours. The strain intermediate in pathogenicity TR4, exhibited an intermediate curve. All four of the viruses grow quite well in the embryo, but clearly the pathogenic strains may be distinguished on the basis of their quantitative effects on the embryo movement and ultimately viability. Also, these results show that viruses which differ in their pathogenicity may be readily distinguished using this system.

The forgoing detailed descriptions and examples are given merely for purposes of illustration. Modifications and variations may be made therein without departing from the spirit and scope of the invention.

Index of Elements Designated by a Numeral

1 egg holder means
2 light source means
3 light intensity sensor means (LISM)
4 determining means
**5*a*** indicator means
**5*b*** recording means
6 light sources
7 eggs
8 phototransistors
9 power supply and signal conditioning means 10 plotter
11 computer
12 analog to digital converter means (ADC means) and digital I/O (input/output) means
13 power control means
14 power source
15 egg incubator means or containment area
16 signal conditioning means
60 computer
61 solid state relay
62 ADC means
64 eggs
65 light box
66 CdS light sensors
68 lights
69 printer

We claim:

1. An apparatus for measuring avian embryo movement, in at least one intact egg comprising:
   egg holder means for holding at least one intact avian egg;
   light source means, operably associated with said egg holder means, for directing light into and through each said at least one intact avian egg, said light being of sufficient intensity and duration to stimulate embryo movement, whereby portions of said light exit each said at least one intact avian egg;
   light intensity sensor means, operably associated with said egg holder means and said light source means, for sensing instantaneous intensities of said portions of said light exiting each said at least one intact avian egg, and;
   determining means, operably associated with said light intensity sensor means, for determining a ratio of range of sensed light intensities to average sensed light intensities, for each said at least one intact avian egg, said ratio being an indication of avian embryo movement.

2. The apparatus of claim 1 further including indicator means, operably associated with said determining means, for indicating said ratio for each said at least one intact avian egg.

3. The apparatus of claim 1 further including recording means, operably associated with said determining means, for recording said instantaneous light intensities and said ratio for each said at least one intact avian egg.

4. The apparatus of claim 1 wherein:
   said light intensity sensor means is a transducer means for providing electrical signals proportional to sensed light intensities, and
   further including signal conditioning means, operably associated with both said light intensity sensor means and said determining means, for conditioning said electrical signals.

5. The apparatus of claim 1 wherein said light intensity sensor means is selected from the group consisting of at least one: Cadmium-Sulfide sensor means, phototransistor, photodiode and photomultiplier tube.

6. The apparatus of claim 1 wherein,
   said egg holder means functions to hold plural intact avian eggs,
   said light source means includes plural light sources for directing light into and through each of said plural intact avian eggs,
   said light intensity sensor means includes plural light intensity sensors for sensing instantaneous intensities of said portions of said light exiting each of said plural intact avian eggs, and
   said determining means functions to determine a said ratio of range of sensed light intensities to average sensed light intensities, for each of said plural intact avian eggs.

7. The apparatus of claim 1 wherein said light source means includes at least one fluorescent light source.

8. The apparatus of claim 1 wherein said egg holder means, light source means and light intensity sensor means, are positioned within an egg incubator means.

9. The apparatus of claim 1 further including,
   control means for controlling operation of said light source means, and
   analog to digital converter means, and digital I/O means, operably associated with both said control means and said light source means.

10. The apparatus of claim 9 wherein said analog to digital converter means, is also operably associated with said light intensity sensor means, and functions to condition and convert analog electrical signals from said light intensity sensor means to digital electrical signals.

11. A process for measuring avian embryo movement in at least one intact egg, comprising:
    directing light into and through at least one intact avian egg, said light being of sufficient intensity and duration to stimulate embryo movement, whereby portions of said light exit each said at least one intact avian egg;
    sensing instantaneous intensities of said portions of said light exiting each said at least one intact avian egg, and;
    determining a ratio of, range of sensed light intensities to average sensed light intensities, for each of said at least one intact avian egg, wherein each said ratio provides a measure of avian embryo movement.

12. The process of claim 11 further including the step of utilizing indicator means to indicate said sensed light intensities and said ratio for each said at least one intact avian egg.

13. The process of claim 11 further including the step of recording said sensed light intensities and said ratio for each said at least one intact avian egg.

14. The process of claim 11 wherein said step of sensing includes positioning adjacent to the shell of each said at least one intact egg a transducer means for providing electrical signals proportional to sensed light intensities, and further including the steps of conditioning electrical signals produced by said transducer means so as to produce conditioned electrical signals, and utilizing said conditioned electrical signals in said step of determining.

15. The process of claim 11 wherein avian embryo movement in a plurality of intact eggs is measured within a time interval of less than ten minutes.

16. The process of claim 11 wherein said step of directing light includes use of at least one fluorescent light source.

17. The process of claim 11 wherein said steps of directing light and sensing intensities are carried out in an egg incubator means.

18. The process of claim 11 wherein each said at least one intact avian egg has an air space, and said step of sensing includes sensing instantaneous intensities of said portions of said light exiting each said at least one intact avian egg just below said air space.

19. The process of claim 11 further including the step of assessing pathogenicity based on change of said ratio with time, and classifying as dead each said at least one intact egg having a said ratio of 0.02 or less.

* * * * *